US007534220B2

(12) United States Patent
Cormier et al.

(10) Patent No.: US 7,534,220 B2
(45) Date of Patent: *May 19, 2009

(54) ADJUSTABLE ERGONOMIC BRACE (75) Inventors: David Cormier, Oxnard, CA (US); Tracy E. Grim, Thousand Oaks, CA (US); Joseph M. Iglesias, Newbury Park, CA (US); Hugo A. Cobar, Tarzana, CA (US); Janelle R. Batman, Pasadena, CA (US); Irving Hu, Camarillo, CA (US); Wendee Lee, Oak Park, CA (US); Jacqueline Jones, Oxnard, CA (US)

(73) Assignee: Ossur hf, Reykjavik (IS)

( * ) Notice: Subject to any disclaimer, the term of this patent is extended or adjusted under 35 U.S.C. 154(b) by 359 days.

This patent is subject to a terminal disclaimer.

(21) Appl. No.: 11/384,630

(22) Filed: Mar. 20, 2006

(65) Prior Publication Data

US 2006/0247565 A1    Nov. 2, 2006

Related U.S. Application Data (63) Continuation-in-part of application No. 10/675,324, filed on Sep. 29, 2003, now Pat. No. 7,037,287.

(51) Int. Cl.
*A61F 5/00* (2006.01)
*F16D 3/00* (2006.01)
*F16B 39/00* (2006.01)
*F16B 39/04* (2006.01)
*F16B 35/00* (2006.01)
*A44B 21/00* (2006.01)
*A61H 3/02* (2006.01)
*A45B 9/00* (2006.01)
*E04H 15/46* (2006.01)

(52) U.S. Cl. .............................. 602/26; 602/16; 602/23; 403/92; 411/81; 411/87; 411/90; 411/393; 24/522; 24/542; 24/707.9; 135/69; 135/75; 135/141; 135/142

(58) Field of Classification Search ................ 602/3, 602/16, 20, 23, 26, 28, 29; 403/92, 93, 95, 403/96; 411/393, 409, 81, 87, 88, 90, 92, 411/93, 96; 24/438, 439, 485, 489–490, 24/494, 498, 522–525, 527, 528, 542, 544, 24/707.9, 708.1, 708.2; 135/65, 69, 75, 141, 135/142; 70/59, 62
See application file for complete search history.

(56) References Cited

U.S. PATENT DOCUMENTS 401,933 A    4/1889    De Camp (Continued)

FOREIGN PATENT DOCUMENTS

EP    1 086 672 A2    3/2001

(Continued)

OTHER PUBLICATIONS www.innovationsports.com website, Sentry and Knee M.D. post-op knee brace, 5 pages (1999).

*Primary Examiner*—Patricia Bianco
*Assistant Examiner*—Keri J Nicholson
(74) *Attorney, Agent, or Firm*—Bacon & Thomas, PLLC (57) ABSTRACT A knee brace is provided with push button actuatable stops, wherein the stops are biased outward into angular locking positions and inwardly directed pressure on the push buttons releases the stops and permits angular adjustment of the stops. A pair of catch plates with locking recesses facing inward, are provided, and outwardly biased locking pins engage the recesses in both catch plates. Each of the stop assemblies has an outwardly directed plate extending over the outer cover plate, and this plate is coupled to the physical stop member around the outer edge of the outer cover plate. The cover plate has angular indicia thereon, which may be viewed through windows in the outwardly extending plate portions of the stop assemblies.

7 Claims, 9 Drawing Sheets

U.S. PATENT DOCUMENTS

| | | | |
|---|---|---|---|
| 2,470,344 A * | 5/1949 | Dzus | 411/548 |
| 2,632,440 A | 3/1953 | Hauser et al. | |
| 3,811,455 A * | 5/1974 | Thur | 135/25.4 |
| 4,239,139 A * | 12/1980 | Bott | 224/324 |
| 4,481,941 A | 11/1984 | Rolfes | |
| 4,520,804 A | 6/1985 | DiGeorge | |
| 4,576,151 A | 3/1986 | Carmichael et al. | |
| 4,620,532 A | 11/1986 | Houswerth | |
| 4,817,588 A | 4/1989 | Bledsoe | |
| 4,886,054 A | 12/1989 | Castillo et al. | |
| 4,982,732 A | 1/1991 | Morris | |
| 5,000,169 A | 3/1991 | Swicegood et al. | |
| 5,135,469 A | 8/1992 | Castillo | |
| 5,409,449 A | 4/1995 | Nebolon | |
| 5,421,810 A | 6/1995 | Davis et al. | |
| 5,437,619 A * | 8/1995 | Malewicz et al. | 602/20 |
| 5,460,599 A | 10/1995 | Davis et al. | |
| 5,611,773 A | 3/1997 | Nash et al. | |
| 5,672,152 A | 9/1997 | Mason et al. | |
| 5,740,054 A | 4/1998 | Durr et al. | |
| 5,814,000 A | 9/1998 | Kilbey | |
| 5,827,208 A | 10/1998 | Mason et al. | |
| 5,873,847 A | 2/1999 | Bennett et al. | |
| 5,921,946 A | 7/1999 | Tillinghast et al. | |
| 5,997,493 A | 12/1999 | Young | |
| 6,045,524 A | 4/2000 | Hayashi et al. | |
| 6,383,156 B1 * | 5/2002 | Enzerink et al. | 602/16 |
| 2006/0155229 A1 | 7/2006 | Ceriani et al. | |
| 2006/0155230 A1 | 7/2006 | Mason et al. | |
| 2006/0155232 A1 | 7/2006 | Ceriani | |

FOREIGN PATENT DOCUMENTS

| | | |
|---|---|---|
| EP | 1086672 A2 * | 3/2001 |
| EP | 1 475 060 A1 | 11/2004 |
| WO | WO 02/02035 A1 | 1/2002 |

* cited by examiner

ADJUSTABLE ERGONOMIC BRACE

CROSS-REFERENCE TO RELATED APPLICATIONS

This is a continuation-in-part of parent application having U.S. Ser. No. 10/675,324, filed Sep. 29, 2003, now U.S. Pat. No. 7,037,287, whose entire contents are hereby incorporated by reference.

FIELD OF THE INVENTION

This invention relates to ergonomic knee braces.

BACKGROUND OF THE INVENTION

In the field of adjustable knee braces or supports, it is desirable that the brace include arrangements for limiting the movement of the lower leg relative to the upper leg both as to bending the knee or flexion, and as to extension of the lower leg relative to the upper leg. Various knee brace arrangements have been proposed, and these have included upper struts for extending along the thigh, and lower struts for extending along the lower leg or calf. These are normally provided both on the inside or medial side of the leg and also on the outer or lateral side of the leg; and the medial and lateral struts are normally padded, and provided with straps to hold them in place. Pivoting arrangements are provided for coupling the upper and lower struts, and stops are provided for limiting both extension and flexion of the knee.

The prior art patents in the field of knee braces include U.S. Pat. No. 5,672,152 granted Sep. 30, 1997; U.S. Pat. No. 5,921,946, granted Jul. 13, 1999; U.S. Pat. No. 4,817,588, granted Apr. 14, 1989, U.S. Pat. No. 4,953,543 granted Sep. 4, 1990, and U.S. Pat. No. 4,620,532 granted Nov. 4, 1986. Although many of the foregoing provided useful results, these prior art knee braces had shortcomings, in that they were unduly bulky, or were not simple to adjust, or did not have as many stop increments as would be desired, or were otherwise not ergonomically configured.

SUMMARY OF THE INVENTION

Accordingly, objects of the invention include providing a knee brace which is compact, easy to use, which has many points of adjustment and is otherwise ergonomically configured. Preferably the adjustments should be simple and natural so that there is no need to resort to collateral written instructions.

Initially, relative to an illustrative preferred embodiment of the present knee brace, the knee brace stop construction operates at the periphery of the pivot arrangements so that the number of stop increments is maximized for the size of the pivot discs. Secondly, the stops may be operated by simple inward pressure on a push button associated with the flexion stop or the extension stop, to release the stop, followed by rotation of the stop to virtually any desired angle, and then followed by release of the push button to permit locking of the stop in the new angular position. With this simplified ergonomic construction, the stop adjustments may be easily made while the brace is mounted on the leg; and the mode of accomplishing stop adjustments is substantially self evident, with the shifting of the stops resulting in the natural or expected angular change in flexion or extension stops.

In order to achieve the foregoing results in one illustrative embodiment, the pivoting assembly interconnecting the upper and lower struts includes, for both extension and flexion, at least one generally circular or arcuate catch plate with stop recesses facing or opening inward toward the center of the assembly, and a movable stop member pivoted at the center of the assembly and having an outwardly biased locking member for selectively engaging one of the stop recesses, and with the locking member attached to a release button which extends radially outward to the periphery of the pivot assembly.

Viewed from a different aspect, the pivoting assembly may include an outer cover or closure plate and an inner cover or closure plate; an arcuately configured array of locking steps; a movable stop member pivoted at the center of the assembly and having an outwardly biased locking member for selectively engaging at least one of the locking steps; and with the locking member attached to a release button which is located radially outward at the periphery of the pivot assembly.

Additional features may include the provision of angular indicia on the outer surface of the outer one of said cover or closure plates and the implementation of the movable stop assembly by an outer, radially extending flat support member adjacent the indicia, preferably with a window through which the angular indicia may be seen. Further, the movable stop assembly may extend over the edge of one of said plates into the space between the two cover plates to cooperate with the locking steps. This construction contributes to the relatively thin overall configuration of the pivoting assembly, which may be only about one-half inch or about 1.3 cm thick. Also, to provide adequate strength and compactness, the brace and it components are preferably made of high strength material such as steel, titanium, zinc alloys, or other high strength metals or high strength plastic.

It is further noted that, in the preferred design, two catch plates are provided, and each of the stop assemblies includes a pin which seats in corresponding recesses in each of the two catch plates, to provide a balanced locking configuration for resisting forces applied between the struts to limit flexion or extension. The inner and outer cover plates may also have complementary recesses to more positively secure the stops at the selected angular position.

Referring back to the overall construction as mentioned above, one strut extends from the knee pivot assembly up the upper leg or thigh, and the other strut extends from the pivot assembly down the lower leg. The pivot stop assembly is mounted on the end of a first one of these struts, and the second strut has stop surfaces on its end adjacent the stop assembly which engage the flexion and extension stops. Further, the catch plates as described above are mounted on opposite sides of this second strut, with the locking member of the movable stop assembly engaging locking steps on both of the two catch plates, so that a balanced positive stopping force is transmitted to the second strut when the stop surfaces on the end of the second strut engage the flexion stop or the extension stop.

Additional aspects of the knee brace may include the following:

(1) catch plates which have separate sets of notches for the flexion and extension stops, and a mechanical coupling between these two sets of notches;

(2) Color coded flexion and extension actuation buttons, with the degree indicia set forth in matching different colors;

(3) Apertures or holes in the actuation buttons to permit locking of the buttons against change.

Other objects, features and advantages of the invention will become apparent from a consideration of the drawings and from the detailed description.

DETAILED DESCRIPTION OF THE PREFERRED EMBODIMENTS

While the specification describes particular embodiments of the present invention, those of ordinary skill can devise variations of the present invention without departing from the inventive concept.

Figure 1:
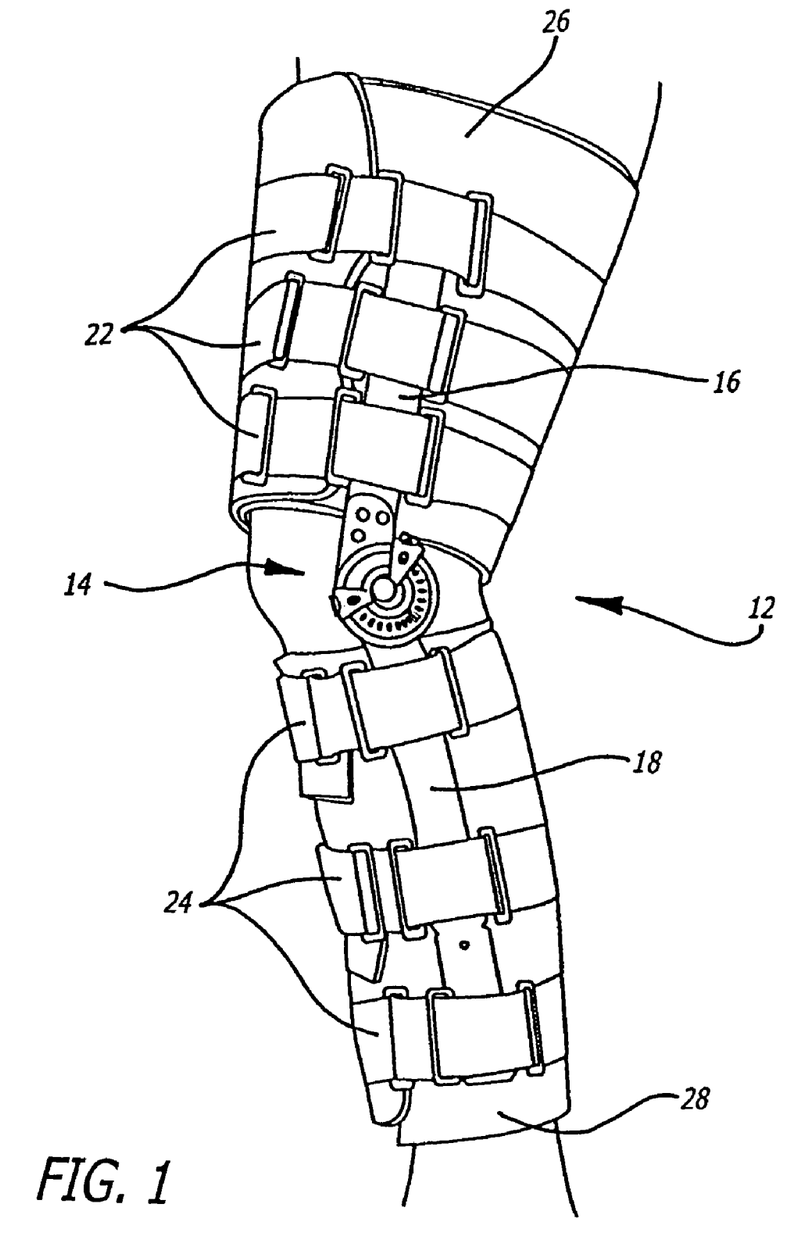
FIG. 1 is a perspective view of a knee brace assembly illustrating the principles of the invention.

Referring more particularly to the drawings, FIG. 1 shows a leg brace 12 for the knee, including two struts extending up and down the leg from a central pivot assembly 14. Extending along the upper leg is a strut 16, and extending down the lower leg from the pivot assembly 14 is a lower strut 18. These struts are sometimes referenced as femoral struts (as extending along the femur or upper leg bone) and tibial struts (extending along the tibia, or the principal lower leg bone). A pivot assembly on the other side of the knee is also provided with struts extending up and down the leg, but these are not visible in FIG. 1.

To hold the struts in place on the leg are a series of straps 22 on the upper leg, and straps 24 on the lower leg. Suitable padding 26 is provided on the upper leg, and the struts are normally secured to the padding 26 by appropriate VEL-CRO® or hook and loop type material. Similar padding 28 underlies the strut 18 and straps 24. The straps 22 extend through the loops 38 to hold the entire assembly together under active usage conditions.

The present invention is directed primarily to the pivot stop assemblies which interconnect the struts. For a post-operative patient, it is desirable to be able to limit the bending of the knee both in the extension direction when the patient is straightening his or her leg, and in the flexion direction where the patient is bending the leg at the knee as far as practical under the circumstances.

The showing of FIG. 1 is of the outside of the left leg. On the inside of the left leg is a similar assembly, to that shown in FIG. 1, with two struts and a central pivot assembly. The two units are similar and both are held the leg by the straps 22 and 24. Most of the parts are common to the inner and outer assemblies, but with the struts and the cover plates being mirror images of one another.

Figure 6:
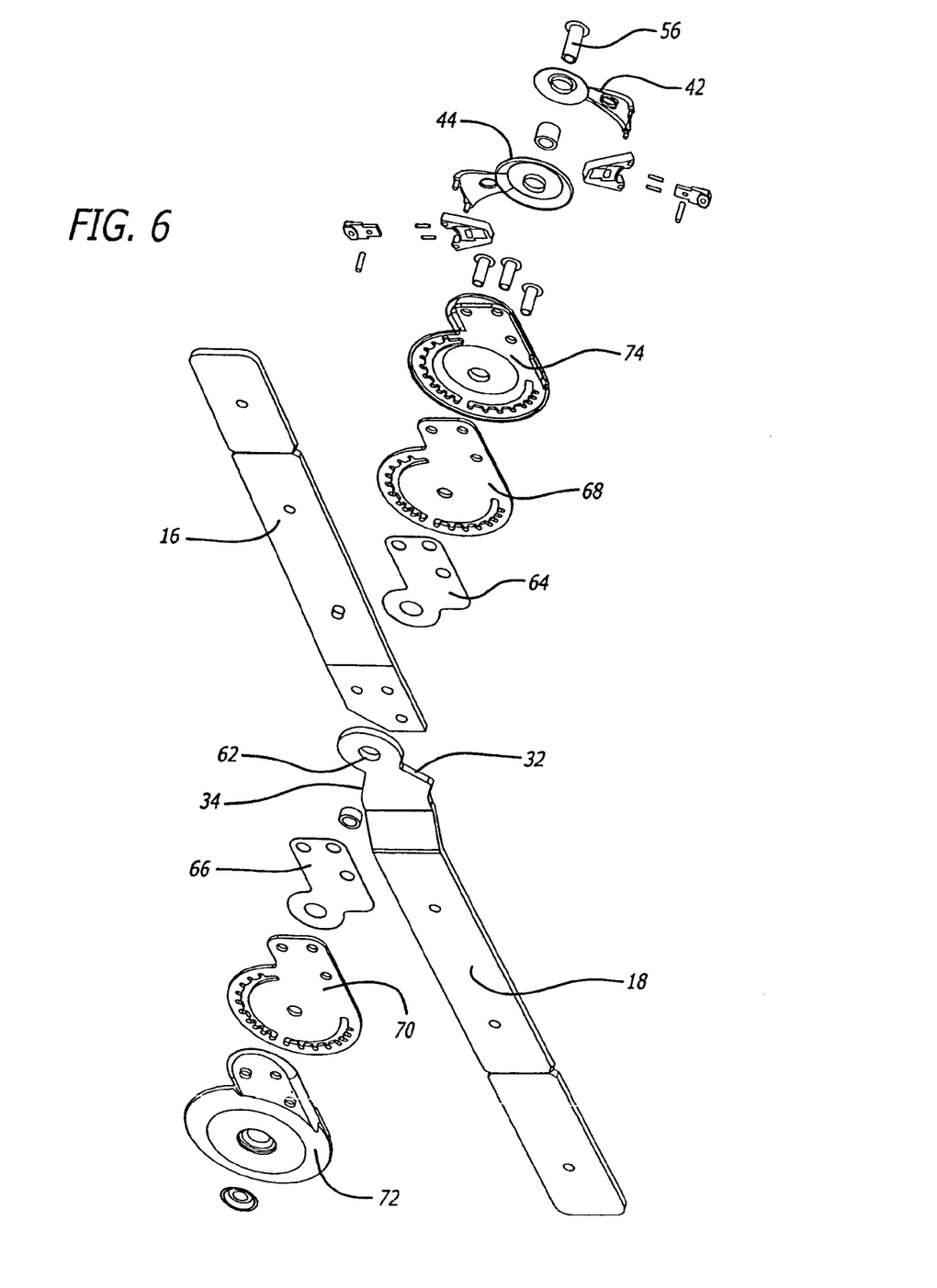
FIG. 6 is an exploded view of the knee brace assembly illustrating the principles of the invention.

To better understand the operation of the entire assembly, it is useful to refer briefly to the exploded view of FIG. 6. In operation, the two struts 16 and 18 are pivoted relative to one another about center rivet 56; and strut 18 has two stop surfaces 32 and 34. Adjustable stops are mounted to the hinge pivot assembly 14 on strut 16 and the adjustable stops engage stop surfaces 32 and 34 to limit pivoting of the knee in both the extension and the flexion directions.

Figure 2:
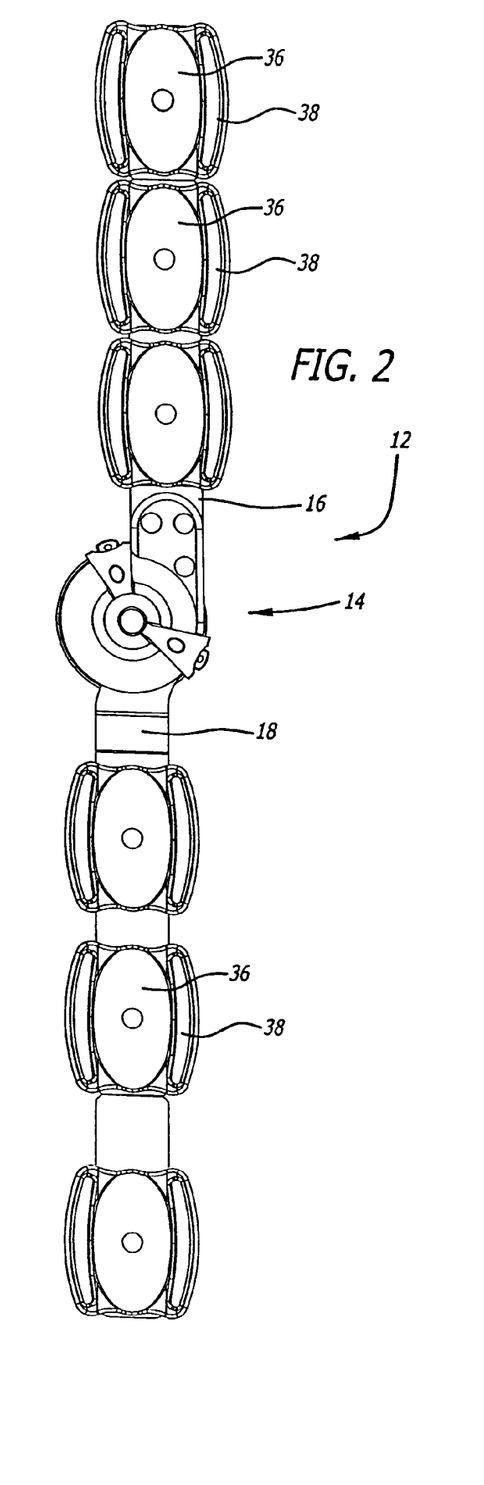
FIG. 2 is a plan view of one of the two knee braces included in the knee brace assembly of FIG. 1.
Figure 3:
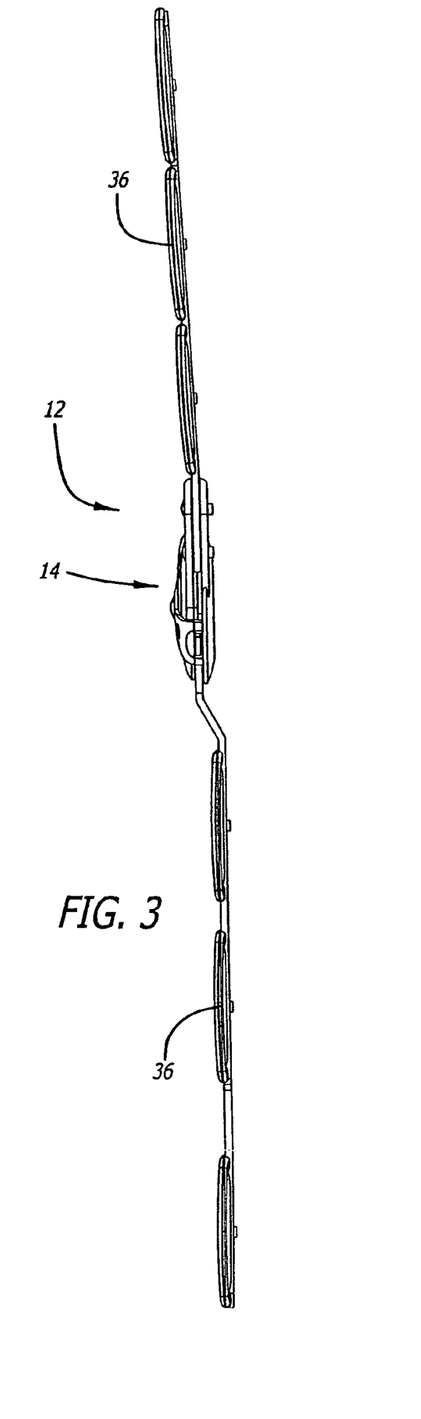
FIG. 3 is a side view of the knee brace of FIG. 2.

FIG. 2 of the drawings shows the assembly 12 and the pivot assembly 14 with the straps 22 and 24, and the padding 26 and 28 removed. Visible in FIG. 2 are the strap coupling members 36 which are secured to the struts, and the strap receiving openings 38. FIG. 3 is a side view of the assembly of FIG. 2. The pivot assembly 14 will be described in greater detail hereinbelow.

Figure 4:
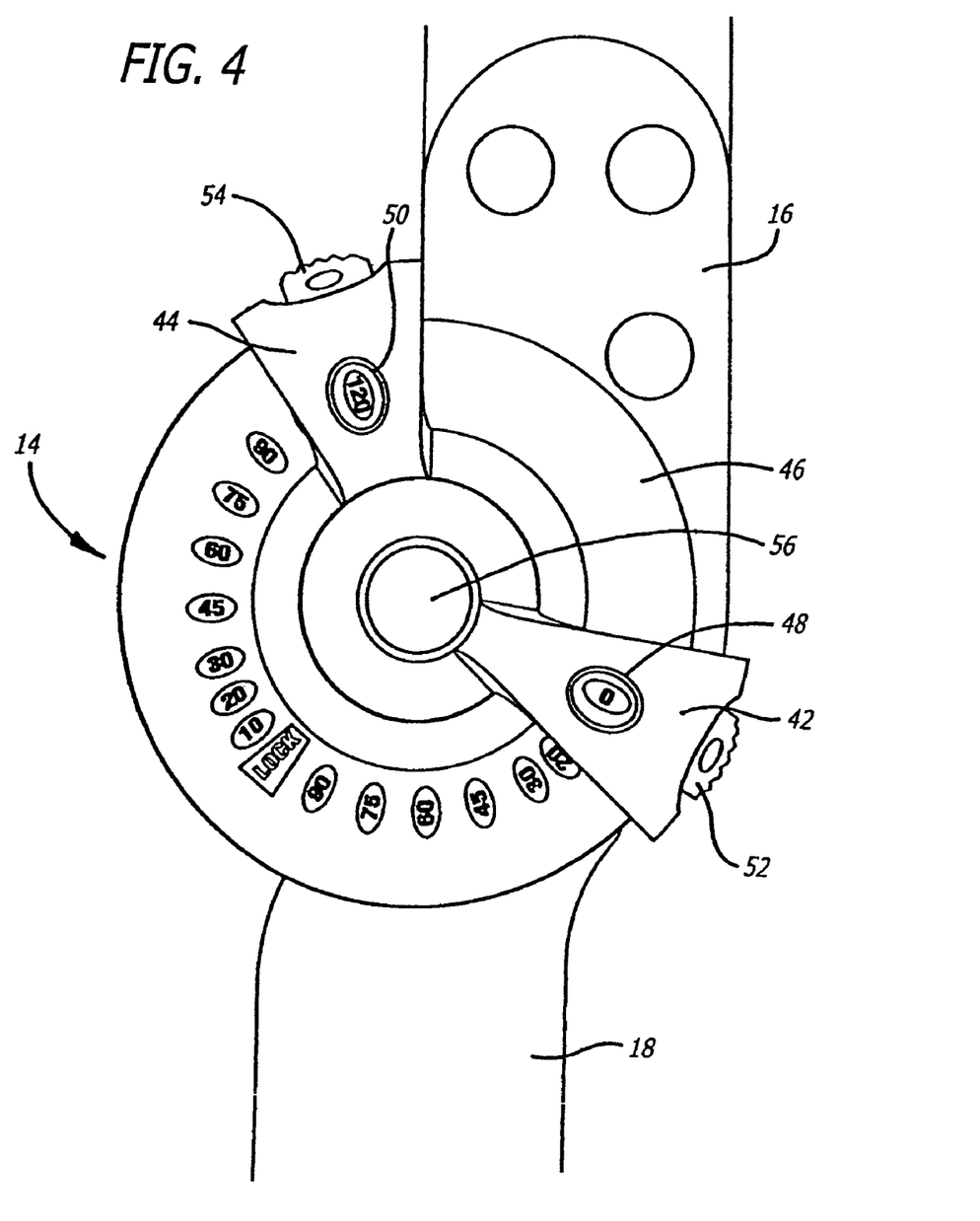
FIG. 4 is an enlarged plan view of a knee brace pivot and motion limiting assembly, illustrating the principles of the invention.
Figure 5:
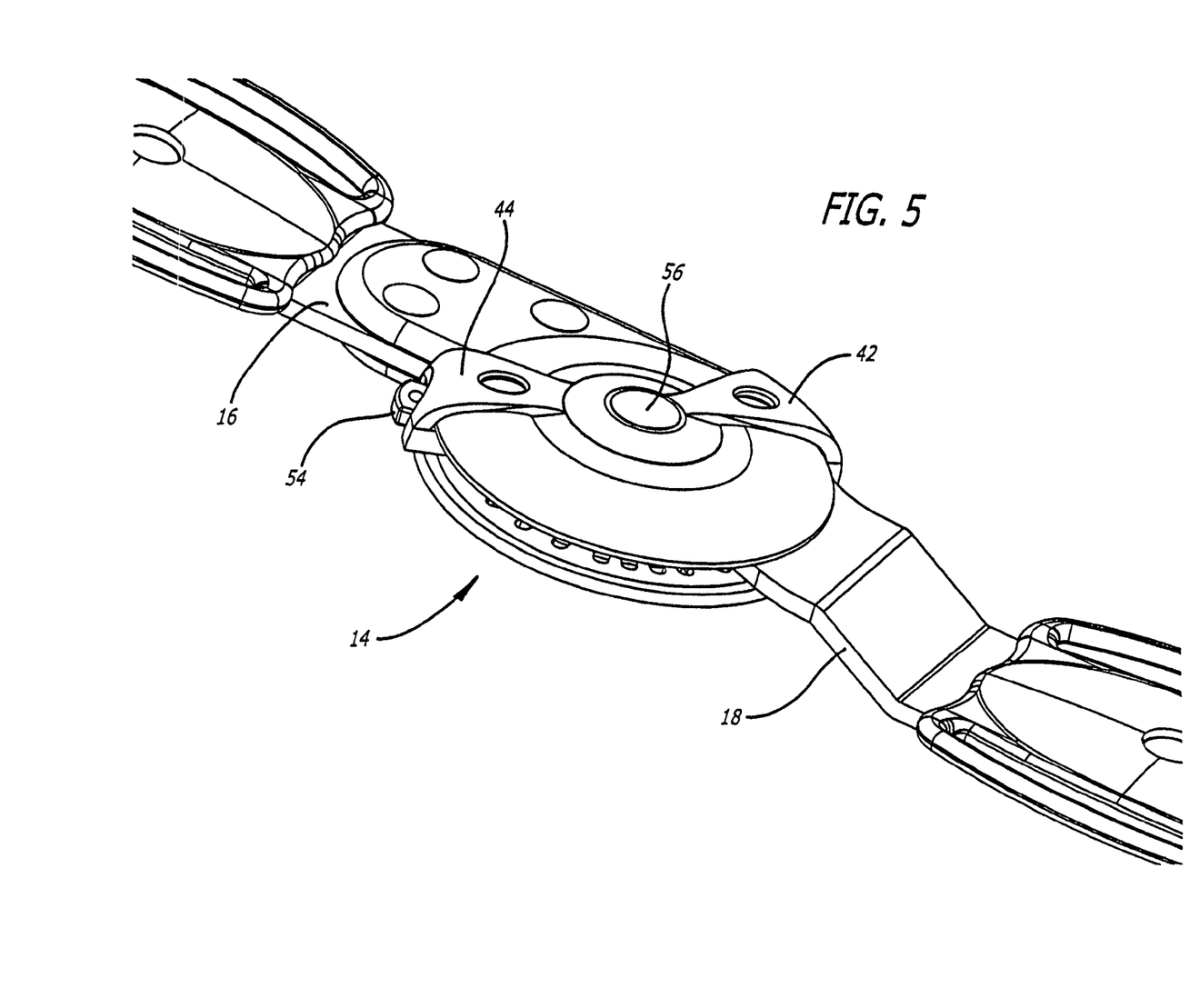
FIG. 5 is an enlarged perspective view of the pivot assembly.

Referring now to FIGS. 4 and 5 of the drawings, these are plan and perspective views, respectively of the pivot assembly 14 which interconnects the struts 16 and 18.

Now, considering FIG. 4 in detail, it includes the extension stop assembly 42 and the flexion stop assembly 44. Visible on the cover plate 46 are degree indicia which may be read through the openings 48 and 50 on the stop assemblies 42 and 44, respectively. To change the limits of motion, the push buttons 52 and 54 are depressed and the stop assemblies are rotated to the desired angular settings. Incidentally, the outermost surfaces of push buttons 52 and 54 are preferably knurled, ribbed or textured for non-slip engagement. Alternatively the stops may be coated with a frictional coating.

Concerning the angular settings, when the extension stop 42 is at zero degrees (0°), the patient is free to fully extend his lower leg. When the extension stop 42 is set to 90°, the lower leg is restrained from movement beyond 90° relative to the upper leg, so the lower leg cannot be straightened out.

Regarding the flexion stop 44, when it is set to 120° the lower leg may be fully bent toward the upper leg. When the flexion stop is set to "lock," then the lower leg is fully extended, and is blocked from any bending. If both stops 42 and 44 are set to 60° for example, the knee is held at 60° from fully open, and is restrained from movement in either direction.

Incidentally, the support members for the stops are both pivoted about the center 56 of the pivot assembly 14, with the reference number 56 representing the head of a rivet extending through the assembly.

Consideration will now be given to the detailed construction of the pivotal stop mechanism, by reference to the exploded view of FIG. 6. As mentioned above, one of the two struts 18 has the two stop surfaces 32 and 34 on its end, and is pivoted, with opening 62 receiving rivet 56 which extends through the entire assembly. The flat parts 64 and 66 are spacers and also serve the function of washers in facilitating rotation of the overlying parts. They may be formed of plastic such as nylon. The catch plates 68 and 70 have a series of inwardly opening recesses which receive outwardly biased locking pins as described below.

The inner cover plate 72 and the outer cover plate 74 may also be provided with inwardly directed recesses, matching those in the catch plates 68 and 70. This provides supplemental restraint for the locking pins shown in detail in later figures of the drawings.

Figure 7:
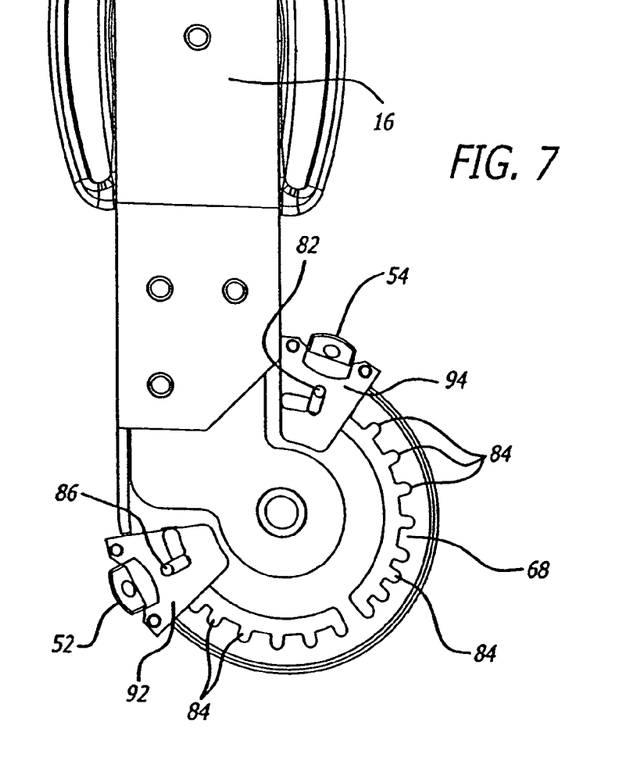
FIG. 7 is an enlarged view of the central pivot and stop assembly of the knee brace of FIGS. 1-6, with the front cover removed.

FIG. 7 is an enlarged view of the central mechanism with one of the cover plates removed. The stop assembly 44 has a locking pin 82 which moves inward with the push button 54 to change settings, but is spring biased outward to engage one of the recesses 84. Similarly, the locking pin 86 associated with push button 52, locks the stop 42 by engagement with a selected one of the catch plate recesses 84.

Figure 8:
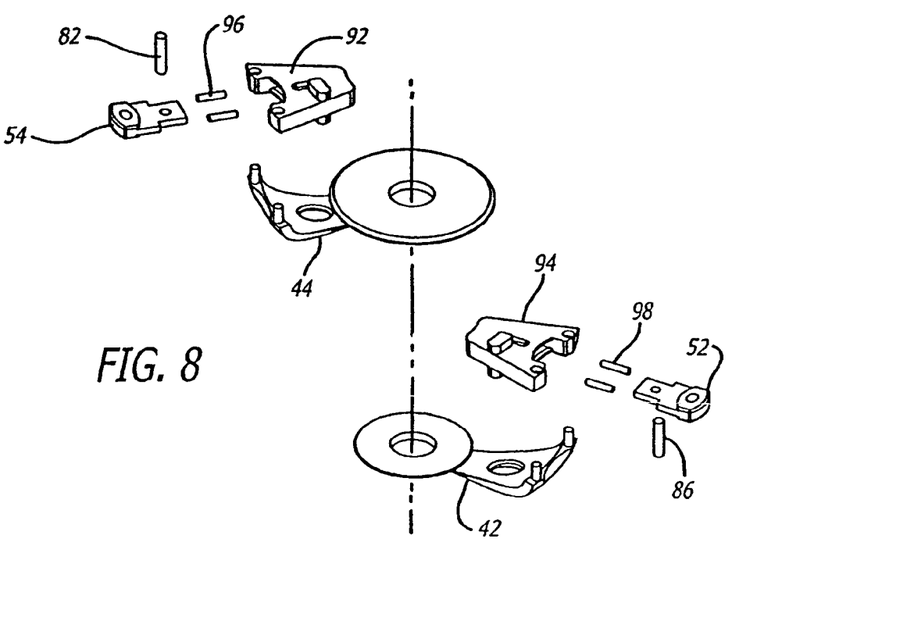
FIG. 8 is an exploded view of the two movable stops and their associated adjustment buttons, and indication support members.

FIG. 8 is an enlarged showing of the physical stop members 92 and 94 which engage the stop surfaces 32 and 34 as shown in FIG. 6. Two small pairs of coil springs 96 and 98 serve to bias the push buttons 52 and 54, and the associated locking pins 86 and 82 outward, into engagement with the catch plate 68 (see FIG. 7) and the other catch plate 70 (see FIG. 6).

Incidentally, the physical stops 92 and 94 may be formed of a high strength zinc alloy referenced as ZA-28, or other high strength material.

Figures 9, 10:
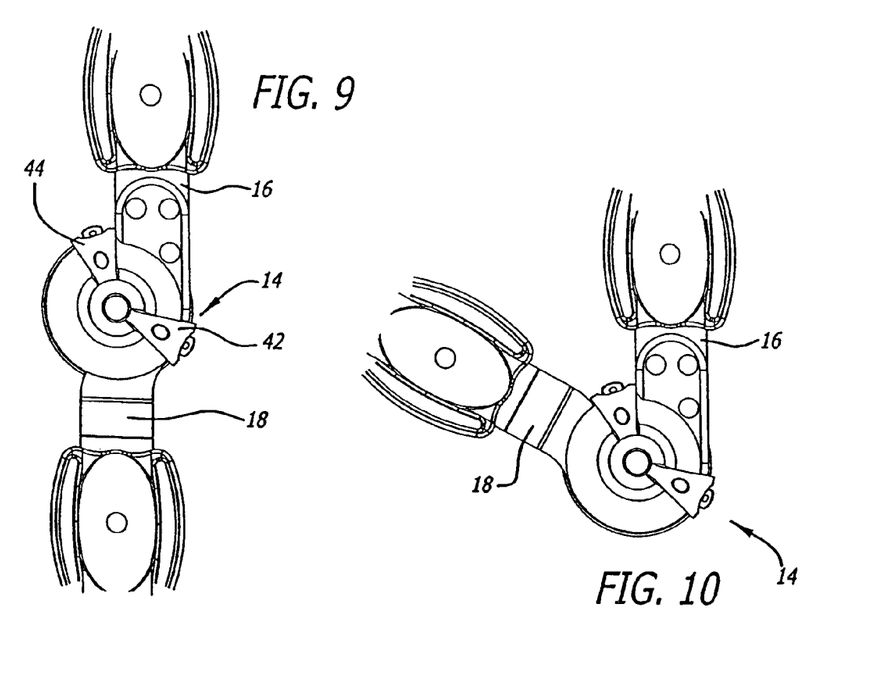
FIGS. 9-12 show various stop adjustment configurations for the knee brace.

FIGS. 9 through 12 shows various adjustments of the stops, and the resultant permitted positions of the struts 16 and 18. More specifically, FIG. 9 shows the extension stop 42 and the flexion stop 44 in their positions for full range of motion, with the extension stop 42 at 0° and the extension stop 44 at 120° (see FIG. 4). In FIG. 9 the struts (and the leg) are fully extended; while in FIG. 10, the struts and the leg are bent to their extreme flexed position, with the two stops in the same positions for both FIG. 9 and FIG. 10.

Figures 11, 12:
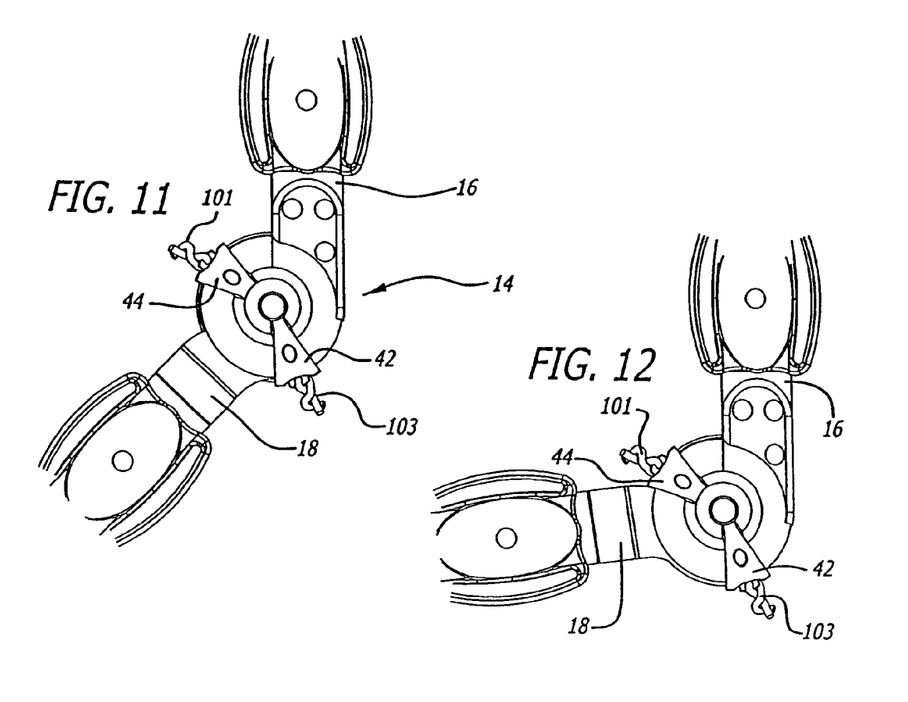

FIG. 11 is a similar pair of drawings with the extension stop at about 45° and the flexion stop at about 75° in both figures. In FIG. 11 the struts are extended as far as possible with this setting of stops 42 and 44; and in FIG. 12 the struts (and leg) are bent as far as permitted with this setting of the stops 42 and 44.

An alternative embodiment of the stop mechanism may include a physical stop having a radially extending slot for receiving a locking pin associated with a push button; and a wire spring biasing the push button and locking pin radially outward relative to the stop support members.

Concerning another matter, with reference to FIG. 4 of the drawings, the push buttons 52 and their associated assemblies are preferably color coded to match colored angle indicia. Thus, push button 52 may be colored blue, with the associated degree indicia from "0" to "90" degrees being the same blue color; and push button 54 and associated indicia may be colored green.

It may be noted that the push buttons are provided with holes near the outer ends thereof. This permits the physician or technical assistant to thread wire or plastic ties through the openings to discourage re-setting or tampering with the angular settings, as shown at reference numerals 101 and 103 in FIGS. 11 and 12 of the drawings. Other elements for preventing or restricting actuation of the push buttons, including locking ties, may be employed; and these elements may be separate from or integral with and movable with respect to, the knee brace assembly.

Figure 13:
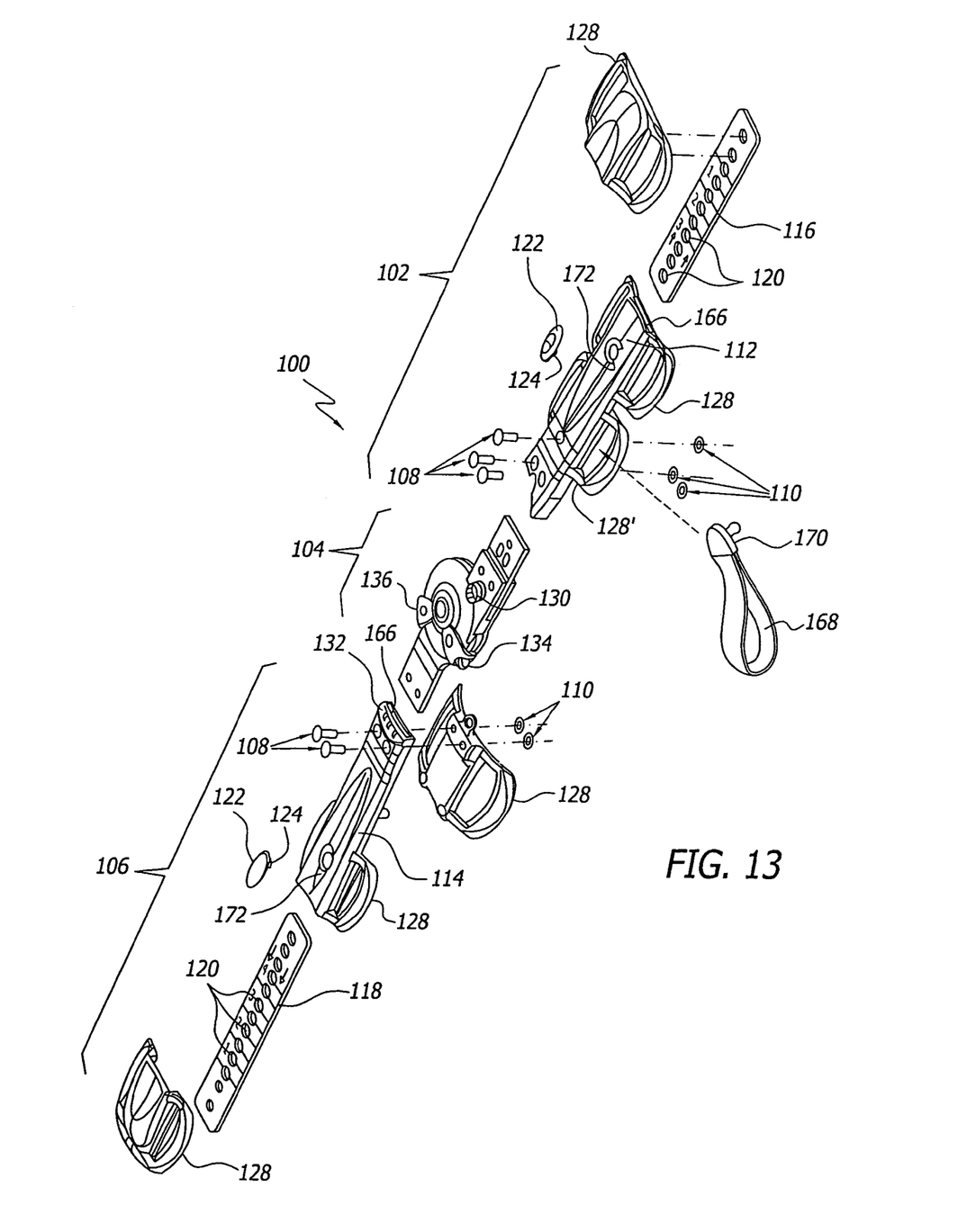
FIG. 13 is an exploded perspective view of an alternative embodiment knee brace assembly.

FIG. 13 is an exploded perspective view of an alternative embodiment ergonomic knee brace having extendable struts 100 for convenient length adjustments. Specifically, in the embodiment shown in FIG. 13, an upper (femoral) strut assembly 102 is joined to a hinge assembly or pivoting arrangement 104. A lower (tibial) strut assembly 106 is also joined to the hinge assembly 104. Each strut assembly 102, 106 is preferably riveted at one end to the hinge assembly 104 via one or more rivets 108 and respective washers and/or lock nuts 110. Other mechanical fasteners or linkages may be used to join the components as well as the use of adhesives, welding, brazing, or the like.

Each strut assembly 102, 106 preferably includes a strut sleeve 112, 114. The strut sleeve 112, 114 is preferably made from a molded plastic having a generally rectangular cross-section with a rectangular channel, slot, or hole 166 extending through the center. The rectangular hole 166 of the strut sleeves 112, 114 is designed to slidably receive respective strut extensions 116, 118. Each strut extension 116, 118 is preferably made from a rigid material such as steel and includes a series of spaced apart length-adjustment holes 120. The preferred elongated flat plate shape of the strut extensions 116, 118 allows the extensions to easily slide in and out of the respective strut sleeves 112, 114 thereby adjusting the overall lengths of the upper and lower strut assemblies 102, 106. As seen in FIG. 13, markings such as numerals, hash marks, and other indicia can be placed on the strut extensions 116, 118 to guide and assist in repeatably and quickly setting up the desired length of the strut assemblies 102, 106.

Once the desired length of the strut extension 116, 118 is found, a screw-in knob or lock lever 122 is turned preferably 180° clockwise manually to lock the strut extension 116, 118 to the respective sleeve 112, 114 thus inhibiting further relative sliding. To do this, the screw-in knob or lock lever 122 includes a post 124 extending underneath having threads thereon that engage threads in the sleeve 112, 114 and that advance the post 124 into one of the adjustment/receiving holes 120 of the respective strut extension 116, 118. This is shown in the cross-sectional view of FIG. 13a. The screw-in lever 122 preferably has a low profile, elongated lever-like shape so that via manual twisting action by the user, sufficient torque is generated to advance the post 124 into the respective strut extension adjustment hole 120. A low profile prevents inadvertent operation of the screw-in lever 122 by accidental brushing against clothing, the wearer's limb, or furniture, for example. For better grip, the upper surface of the lever 122 may be textured.

Figure 13A:
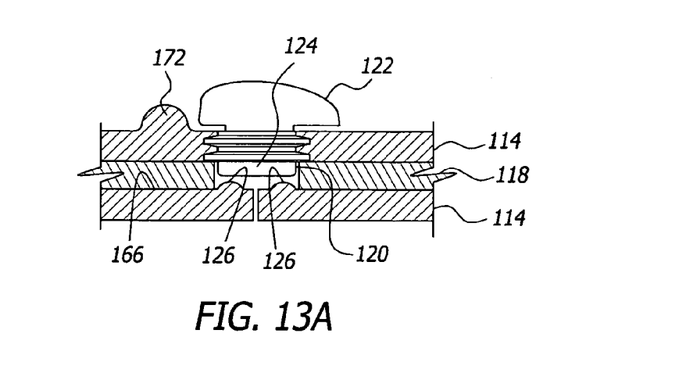
FIG. 13a is a cross-sectional view showing the interaction of the detent and the adjustment hole of the strut extension.

To unlock the strut extension 116, 118 from the strut sleeve 112, 114, an opposite turn of the screw-in lever 122 withdraws the post 124 from engagement with the hole 120. The strut extension and its sleeve can now freely slide relative to each other.

To provide sufficient strength, the screw-in lever 122 and strut sleeves 112, 114 are preferably made from glass filled nylon or like polymers. The strut sleeves may have an aluminum, steel, or like metal skeleton over which the plastic is molded if more strength is desired.

Because the adjustment holes 120 of the strut extensions 116, 118 are covered by the strut sleeves 112, 114 when the two parts are assembled, the user or wearer is not able to easily align the post 124 with the desired adjustment hole 120 to interlock the sleeve and extension together. To enhance easy alignment of the post 124 and adjustment hole 120, the preferred embodiment strut sleeve 112, 114 has one or more detents 126 formed into the interior surface at the bottom of the rectangular opening 166. This is shown in the cross-sectional view in FIG. 13a.

Therefore, as each adjustment hole 120 slides past the detent 126, there is a noticeable click-stop that can be felt and heard by the user indicating that the post 124 and one of the adjustment holes 120 are aligned. In the preferred embodiment, the detent 126 is a bump, ridge, ramp, or like click-stop that slightly enters and easily slides out of any one of the adjustment holes 120 of the strut extension 116, 118. Preferably, the detent 126 is formed from the material used to create the strut sleeve 112, 114, and more preferably, the detent 126 is a partial cutout of the sleeve bottom to form a cantilevered spring configuration shown in FIG. 13a. That is, the detent 126 is an inward facing bump positioned at the end of an elongated, rectangular spring board whose shape is defined by three-quarters peripheral cut with a base still attached to the sleeve 112, 114. This cantilevered spring configuration for the detent 126 creates even greater vertical compliance allowing the bump of the detent 126 to engage and disengage the adjustment hole 120 for improved tactile and audible indications yet does not significantly impede the strut extension sliding action inside the strut sleeve 112, 114. One or more detents 126 may be used in each sleeve and/or for each hole.

To prevent the user from accidentally overly twisting the screw-in lever 122, an optional turn stop 172 positioned on the surface of the sleeve 112, 114 blocks the outer limit of rotational travel of the screw-in lever 122. FIGS. 13 and 13a show such a stop 172. The preferred embodiment turn stop 172 has a ramp-like profile with a flat engagement face that is designed to engage the rotating screw-in lever 122. Thus, the screw-in lever 122 as shown in FIG. 13 can be rotated clockwise through about 270° and more preferably about 180° of travel until encountering the rising resistance of moving up the ramp of the turn stop 172, and the screw-in lever 122 can be rotated about 270° and more preferably about 180° counterclockwise until it encounters the flat engagement face at the opposite side of the turn stop 172. The pitch of the threads for the post 124 is selected so that about a 270° and more preferably about 180° clockwise turn is sufficient to fully engage the post 124 with the adjustment hole 120. Of course, smaller or larger angular turns of the screw-in lever 122 to lock and unlock the components are contemplated. The preferred 180° rotational range to lock/unlock the screw-in lever 122 is selected for ergonomics and ease of use of the knee brace wearer.

Although in the exemplary embodiment shown the detent engages the strut extension and adjustment holes from the bottom of the sleeve, it is possible to have detents that engage the strut extension and adjustment holes from the top or from the side, assuming the edge of the strut extension has been cut or formed with a series of notches, pits, or indentations to achieve the click-stop action.

An assortment of curled cuffs 128 optionally having laterally extending D-rings can be mounted, fastened, molded, or glued to the strut assemblies 102, 106. In the exemplary embodiment shown in FIG. 13, a single cuff 128 is fastened to the very distal end of the upper strut extension 116, and likewise a cuff 128 is attached to the distal end of the lower strut extension 118. The upper strut sleeve 112 includes two cuffs 128 molded integrally with the sleeve while the lower strut sleeve 114 has a cuff 128 molded integrally with the sleeve with a second cuff that can be attached thereto. Adjustable straps (not shown) with VELCRO® fasteners, buckles, and the like can then be looped through the D-rings of the cuffs 128. The straps are used to attach the knee brace to the patient's leg. The large surface area of the cuffs 128 helps with fitment of the ergonomic knee brace 100 to the patient's leg and minimizes shifting of the leg within the knee brace. Optionally, a gastrocnemius strap 168 with a snap 170 at one end is provided with the knee brace 100. The snap 170 selectively attaches the gastrocnemius strap 168 to an eyelet or blind hole in the strut sleeve 112, and more precisely to the superior or calf cuff 128'. When attached to the strut sleeve 112, the strap 168 is worn around the calf area of the patient's leg and helps suspend the knee brace 100 to the leg.

The alternative embodiment knee brace shown in FIG. 13 further includes a drop lock feature that can quickly and easily lock down the relative pivoting motions of the upper and lower strut assemblies 102, 106. Specifically, a sliding drop lock button 130 is preferably located on the hinge assembly 104 that when slid into its locking position, it interlocks the upper and lower strut assemblies 102, 106 to inhibit the pivoting action.

To quickly and repeatably locate the desired flexion angle of the knee when the drop lock can be used, the lower strut sleeve 114 optionally has a sloped face 132 opposite to the location of the drop lock button 130, essentially on opposite sides of the hinge assembly 104. This arrangement provides a sloped face 132 with flexion angle markings that are visible to the wearer of the knee brace or to a nurse when he or she looks downward on the knee brace 100 when locking down the pivoting action with the drop lock button 130. As in the previous embodiments, the hinge assembly 104 includes a flexion stop 134 and an extension stop 136 that sweep about the hinge assembly 104. With the drop lock button 130 disengaged, the upper and lower strut assemblies 102, 106 are free to pivot within the defined angular limits set by the flexion and extension stops 134, 136. Advantageously, the pivoting-action-lockout via the drop lock button 130 and the flexion and extension stops 134, 136 are all centrally congregated at the hinge assembly 104.

Figure 14:
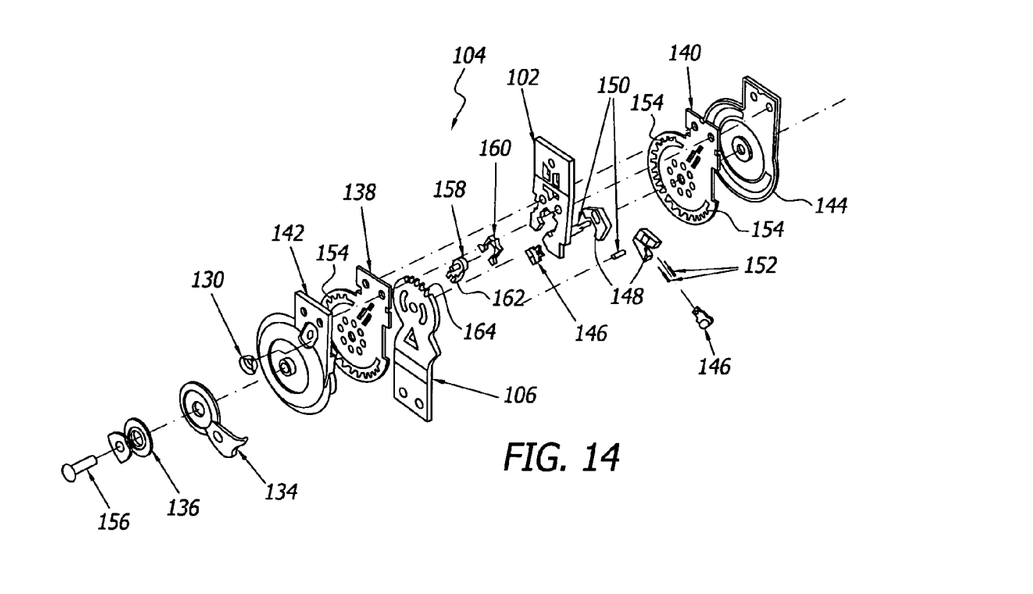
FIG. 14 is an exploded perspective view of the hinge assembly for the knee brace shown in FIG. 13.

FIG. 14 is an exploded perspective view of the hinge assembly 104 from the alternative embodiment knee brace shown in FIG. 13. The principle of operation of the flexion and extension stops 134, 136 are as described in the preceding embodiments. As seen in the exploded view of FIG. 14, the hinge assembly 104 is a collection of preferably two disk-like catch plates 138, 140. Each catch plate 138, 140 has a series of recesses or teeth 154 located at the outer periphery of circumferentially extending, arcuate-shaped slots. The catch plates 138, 140 are mounted to the proximal ends of the lower strut assembly 106 and the upper strut assembly 102. The remaining structures of the respective strut assemblies have been omitted from FIG. 14 for ease of illustration. Both proximal ends of the lower strut assembly 106 and the upper strut assembly 102 freely pivot against each other. The internal workings of the hinge assembly 104 are enclosed by an outer cover plate 142 and an inner cover plate 144. The flexion stop 134 and the extension stop 136 are mounted to the hinge assembly 104, and each extension or flexion stop 134, 136 has a stop release button 146 that is biased by a spring 152 away from a stop base 148 wherein a lock pin 150 extending through the stop base 148 selectively engages to the teeth 154 formed in the catch plates 138, 140. By pushing radially inward on the extension or flexion stop release button 146 against the bias of the spring 152, the lock pin 150 is disengaged from the teeth 154 allowing the extension or flexion stop base 148 to be moved along the circumferential slots formed in the catch plates 138, 140. This movement enables adjustment the flexion or extension stop angles. Once the finger pressure is released from the extension or flexion stop release button 146, the spring bias forces the lock pins 150 radially outward to again engage the teeth 154 in the catch plates 138, 140. A center rivet 156 acts as a hub for the hinge assembly 104 and holds the entire assembly together.

FIG. 14 also shows the preferred construction of the drop lock button 130 that is slidably mounted to the surface of the outer cover plate 142. The drop lock button 130 engages a drop lock base 158 which is held in place by a horseshoe shaped spring 160, which components are then fit into the upper strut assembly 102 as shown. One or more ribs 162 extend from the drop lock base 158. The ribs 162 selectively engage one or more stop recesses or teeth 164 formed at the proximal end of the lower strut assembly 106. Thus, by sliding the drop lock button 130 radially inward or outward, the drop lock base 158 moves toward or away from the teeth 164 thereby engaging or disengaging the ribs 162 with the teeth 164. If engaged, the engage between ribs 162 and teeth 164 interlocks the lower strut assembly 106 to the upper strut assembly 102 thereby inhibiting the relative pivoting action of the two components. The horseshoe spring 160 pinches on the drop lock base 158 to provide some bias to hold the drop lock base 158 in either the engaged or disengaged positions.

It is to be understood that the foregoing detailed description discloses one preferred illustrative embodiment of the invention. Various changes and modifications may be made without departing from the spirit and scope of the invention. Thus, by way of example and not of limitation, instead of having catch plates with locking recesses, a series of outwardly extending rods or protrusions may be provided, with the stop buttons having an outwardly biased fork member for engaging the rods and thereby positioning the stop body or stop plate in the desired angular position. In addition, while the disclosed configuration of the stop supports 44 and 48 is preferred, the stop assemblies may be pivotally mounted within the cover plates as well as, or instead of, extending over the outer surface of the outer cover plate. With regard to another matter, the release push button may be integral with the physical stops. Also, the various parts may be replaced by their mechanical equivalents, such as rivets being replaced by threaded fasteners, or the like. Accordingly, the present invention is not limited to the precise embodiments described in detail hereinabove, and shown in the accompanied drawings.

What is claimed is:

1. An ergonomic brace comprising:
   a first elongate strut;
   a second elongate strut;
   pivoting arrangements for intercoupling said first strut and said second strut; said pivoting arrangements having a center; and
   said pivoting arrangements including stop assemblies both for flexion and extension, including;
   a) a catch plate formed of a flat arcuate disc having an arcuate opening and having stop recesses facing or opening toward the center of said pivoting arrangements;
   b) a movable stop pivoted at the center of the assembly and having an outwardly biased locking member for engaging said stop recesses, coupled to a release button which extends radially outward to the periphery of said pivoting arrangements; and
   c) said release button being movable inward to shift said locking member out of said stop recesses to permit angular adjustment of said stop;
   at least one of said struts having a flexion stop surface for engaging the flexion stop assembly;
   at least one of said struts having an extension stop surface for engaging the extension stop assembly; and
   an extension slidably engaging and extending over at least one of said first strut and second strut, wherein the extension includes a screw-in lock engaging one of a plurality of receiving holes in the at least one of said first strut and second strut;
   wherein the screw-in lock includes a rotating lever having a threaded post screwed to respective threads formed within the thickness of the extension and the extension defining an outer surface forming a ramped turn stop arranged to selectively engage the lever such that the rotating lever encounters rising resistance while moving up the turn stop in a first rotational direction until encountering a flat engagement face formed at one side of the turn stop to prevent further rotation of the rotating lever in the first rotational direction.

2. An ergonomic brace of claim 1, wherein said extension at a location opposite to the screw-in lock includes a detent engaging at least one of the receiving holes.

3. An ergonomic brace of claim 2, wherein said extension includes a resilient polymer material, and said detent is formed from a partially cut out portion of the resilient polymer material.

4. An ergonomic brace of claim 1, wherein said extension includes a curved cuff having at least one D-ring.

5. An ergonomic brace of claim 1, wherein said extension includes a looped, gastrocnemius strap detachably engaging said extension.

6. An ergonomic brace of claim 1, wherein an end of at least one of said first and second struts near the center of the pivoting arrangements includes a sloped face having markings.

7. An ergonomic brace comprising:
   a first elongate strut having a plurality of receiving holes generally arranged along at least a portion of the longitudinal length thereof; and
   an extension slidably engaging and extending over the first strut, said extension including a rotatably advancing, threaded lock engaging at least one of a plurality of receiving holes of the first strut, the extension forming upper and lower segments positioned parallel and adjacent to the fist strut, and the lower extension segment having an inner surface defining a cantilevered detent stop formed from a partially cut out portion at a location opposite the lock and selectively engaging at least one of said receiving holes;
   wherein the threaded lock includes a rotating lever having a threaded post screwed to respective threads formed within the thickness of the upper extension segment, and the upper extension segment having an outer surface forming a ramped turn stop arranged to selectively engage the lever such that the rotating lever encounters rising resistance while moving up the turn stop in a first rotational direction until encountering a flat engagement face formed at one side of the turn stop to prevent further rotation of the rotating lever in the first rotational direction.

\* \* \* \* \*